(12) United States Patent
Khouri

(10) Patent No.: US 6,514,200 B1
(45) Date of Patent: Feb. 4, 2003

(54) PATIENT COMPLIANCE MONITOR

(75) Inventor: Roger K. Khouri, Key Biscayne, FL (US)

(73) Assignee: Brava, LLC, Coconut Grove, FL (US)

( * ) Notice: Subject to any disclaimer, the term of this patent is extended or adjusted under 35 U.S.C. 154(b) by 0 days.

(21) Appl. No.: 09/572,348

(22) Filed: May 17, 2000

(51) Int. Cl.[7] .......................... A61B 5/00; A61B 16/16; A61F 5/00
(52) U.S. Cl. .................. 600/300; 600/38; 600/587; 128/898; 128/920; 606/6
(58) Field of Search ................. 600/300, 301, 600/309, 365, 481–486, 500, 503, 558, 559, 587–592, 38–41; 128/898, 847, 903, 904, 920–925; 601/14, 6; 602/36–38; 606/191–194, 196–199

(56) References Cited

U.S. PATENT DOCUMENTS

| | | | |
|---|---|---|---|
| 4,612,937 A | * 9/1986 | Miller | ......................... 600/455 |
| 4,832,033 A | 5/1989 | Maher et al. | |
| 5,536,233 A | 7/1996 | Khouri | |
| 5,662,583 A | 9/1997 | Khouri | |
| 5,676,634 A | 10/1997 | Khouri | |
| 5,695,445 A | * 12/1997 | Khouri | ......................... 600/38 |
| 5,701,917 A | 12/1997 | Khouri | |
| 5,827,180 A | 10/1998 | Goodman | |
| 5,931,783 A | * 8/1999 | Redano | ......................... 600/439 |
| 5,950,632 A | 9/1999 | Reber et al. | |
| 6,042,537 A | * 3/2000 | Kaiser | |
| 6,083,912 A | 7/2000 | Khouri | |
| 6,290,662 B1 | * 9/2001 | Morris et al. | ............... 601/149 |

* cited by examiner

Primary Examiner—Max F. Hindenburg
Assistant Examiner—Michael Astorino
(74) Attorney, Agent, or Firm—Thompson Coburn, LLP

(57) ABSTRACT

A patient monitoring device includes a microprocessor controller having a clock circuit and memory coupled to one or more sensors physically carried by a medical appliance such that as the medical appliance is properly fitted to and worn by the patient, the sensors provide an electrical signal confirming that which may be then timed to provide data which confirms a patient's compliance with a recommended protocol. By combining and correlating the sensor data with the clock or timer provided as part of the controller, a time chart of data may be created indicating when and for how long the patient actually wears the device. Additionally, other sensors may be used to collect data relating to various operational parameters of the device including the amount of negative pressure presented under a vacuum dome or other parameters related to the operation of the medical appliance itself, as desired.

10 Claims, 1 Drawing Sheet

PATIENT COMPLIANCE MONITOR

CROSS REFERENCE TO RELATED APPLICATIONS AND PATENTS

This application is related to, but does not claim priority from, the following related applications and patents naming the inventor as an inventor thereof:

U.S. Pat. No. 5,536,233; U.S. Pat. No. 5,662,583; U.S. Pat. No. 5,676,634; U.S. Pat. No. 5,695,445; U.S. Pat. No. 5,701,917; U.S. patent application Ser. No. 09/203,832 and U.S. patent application Ser. No. 09/141,460; the disclosures of which are incorporated herein by reference.

BACKGROUND OF THE INVENTION

There are numerous instances where persons desire enlargement of the soft tissue in their bodies. The inventor herein has worked extensively in this area by inventing and patenting various devices and methods for growing and enlarging soft tissue through different means. Generally, these devices have been focused on enlarging a woman's breasts, although other various applications have also been disclosed and described in the inventor's prior patent filings. Also, generally, these inventions operate under a principal of applying a controlled tension to a patient's soft tissue such as by applying a vacuum, or through a mechanical structure which induces a tension. Various problems have been solved by the inventor in inventing these devices, many of which have contributed to the efficacy and suitability of these devices for application to a human patient. Various embodiments of these devices have been demonstrated through various trials to be effective when used in a prescribed manner.

A problem which exists universally, and which the inventor herein has encountered with his various inventions, is that of patient compliance. Even the best of medical devices can be rendered ineffective or produce less than desirable results should the patient fail to use the device in the manner in which it is prescribed. In particular, it is anticipated that the inventor's devices will be prescribed by a medical practitioner for a patient's wear using a protocol relating to wear times and pressures induced or tensions exerted in the soft tissue. It is expected that a medical practitioner will be able to judge these after a careful examination of the patient and through selection of a prescribed treatment regimen. Although this information will be reliably communicated to a patient, at present there is little guarantee that a patient will indeed follow that prescribed regimen to thus achieve desirable results.

In order to solve these and other problems in the prior art, the inventor herein has succeeded in designing and developing a patient monitoring device which may be readily integrated into a control for any of the inventor's prior embodiments of a soft tissue enlargement device. This patient monitoring device can include a microprocessor controller having a memory and being linked to one or more sensors. These sensors may sense for example a temperature reading such that when the device is placed adjacent the patient's soft tissue, the patient's natural body heat is sensed by the temperature sensor to thereby indicate that the device is being properly worn. Still another possibility for a sensor includes a pressure sensor which can be placed in any of the vacuum lines or under the vacuum domes provided as part of the soft tissue enlargement device to sense when the pump which draws the negative pressure or vacuum has indeed created such a negative pressure or vacuum. This indicates that the patient is indeed wearing the device as the vacuum or negative pressure is created between the device and the patient's soft tissue. Still another sensor, a third sensor, could also be coupled to the microprocessor controller and provide an additional input of a differential nature, e.g., pressure taken at a different part of the device, or another temperature sensor, or any other convenient parameter which may be monitored and which will provide an indication that the patient is indeed wearing the device as prescribed. For example, a mechanical push button or snap switch having a relatively light pressure actuator may be conveniently placed in a strap or other part of the device which would be actuated as the device would be fastened or secured properly to the patient's body. Other types of sensors could be thought of by those of skill in the art as would be appropriate to the particular device and application.

By using a microprocessor controller, a clock and memory may be provided as part of the controller or in separate microchips so that the length of time that the sensor is above a preselected threshold can be determined and indicate the amount of time that the patient has been wearing the soft tissue enlargement device. Thus, the amount of time that the soft tissue enlargement device remains unworn may be readily determined as well as the amount of time that the device is being worn, and these times may also be indexed to a time of day to provide an additional degree of reliability for the data being collected. As with any typical microprocessor controller, an output port of the controller may be used to communicate the data to another computer, a display such as a computer monitor, a printer, or other recorder as might be desired to collect the data. In still other applications, it might be desired to telecommunicate the data collected by the patient monitor through a communication link such as through a LAN, WAN, or even the Internet.

While the principal advantages and features of the invention have been described above, a fuller understanding of the invention may be attained by referring to the drawings and detailed description of the preferred embodiment which follows.

BRIEF DESCRIPTION OF THE DRAWING

The drawing is a schematic block diagram of the patient compliance monitoring device of the present invention.

BRIEF DESCRIPTION OF THE PREFERRED EMBODIMENT

Figure 1:
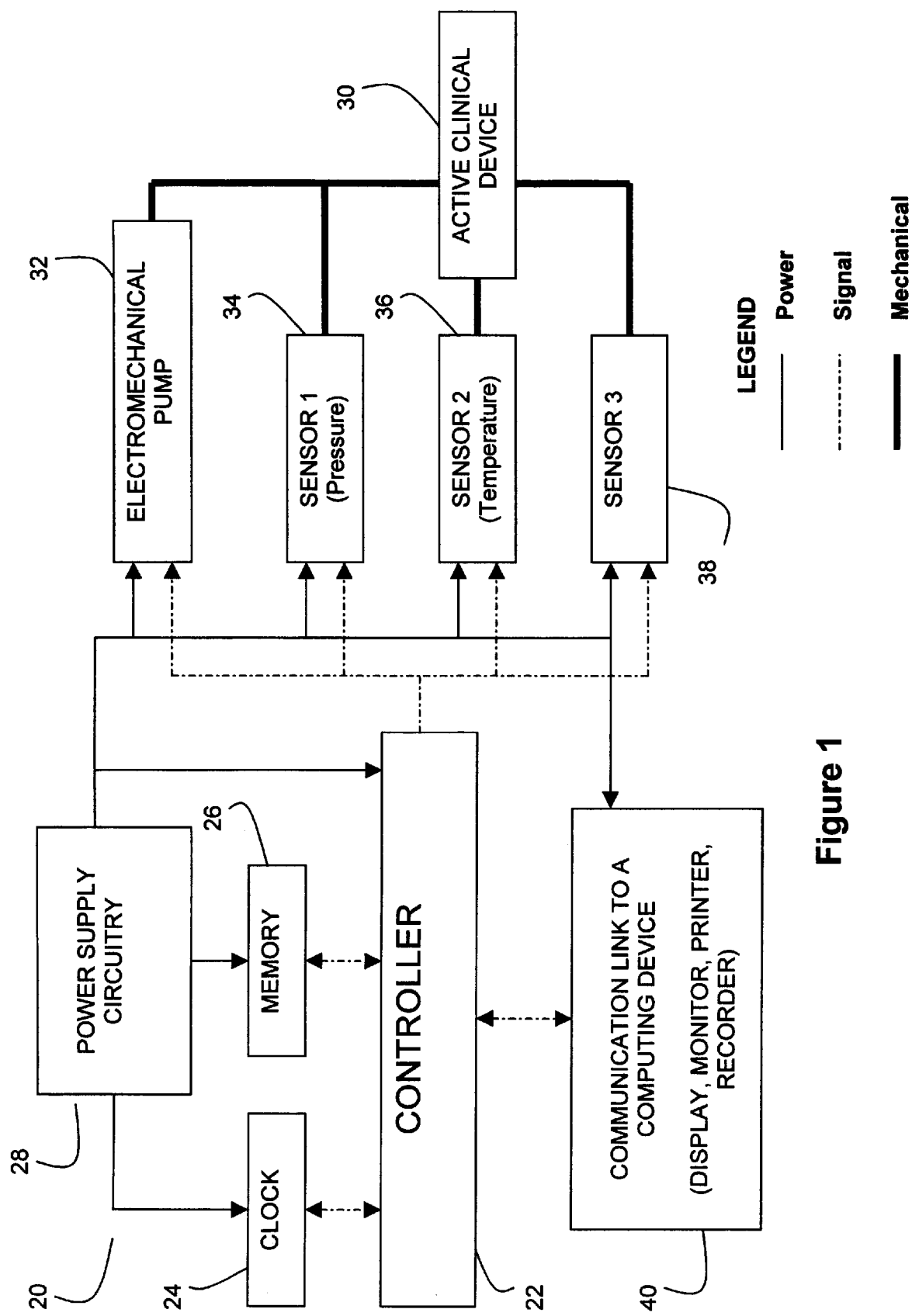

The patient compliance monitoring device 20 of the present invention is shown in the figure to include a controller 22 which may be a microprocessor, microcomputer, digital logic device, PAL, or other such suitable controller including one as may be embodied in an ASIC, as would be known to those of skill in the art. A clock or timing circuit 24 and memory 26 may be separately provided or provided as part of controller 22 as desired and appropriate under the circumstances of the particular devices chosen to embody these functions. However, this is considered to be a matter of design choice and not significant with respect to the operation or best mode choice for the present invention. Similarly, a power supply circuit 28 is shown and may include a battery with wave form smoothing or filtering again as would be known to those of skill in the art. The active clinical device 30 may be considered as a soft tissue enlargement device as shown in any of the inventor's prior patent filings such as those which disclose a pair of vacuum domes for enclosing the breasts of a female patient. An electromechanical pump 32 may be provided and used to draw a negative pressure within the domes of the active clinical device 30 to apply the protocol as prescribed for enlarging soft tissue. Various embodiments of these devices may be found in the inventor's prior patent filings and it is not considered to be significant for purposes of enablement or best mode that any one or the other of these structures be utilized as long as they are chosen with care by one of ordinary skill in the art. A first sensor 34 may be mechanically mounted within the active clinical device 30 and used to sense the pressure, or negative pressure as the case may be, exerted by the active clinical device 30 over the soft tissue desired to be enlarged, as taught by the inventor previously. The particular location chosen for placement of the sensor 34 is considered to be a matter of design choice. However, it may be placed conveniently in any of the vacuum lines associated with the electromechanical pump 32, underneath either of the two vacuum domes, or elsewhere as desired and which may be determined with minimal experimentation to provide the most reliable sensor readings. A second sensor 36 may also be physically mounted to the active clinical device 30 and may be placed anywhere as convenient to come in contact with the patient's skin or other soft tissue such that it is heated by the patient's body as the active clinical device 30 is worn. Thus, as the active clinical device 30 is used, the temperature sensor 36 senses an elevated temperature over room temperature and provides a reliable indication that the patient is indeed wearing the active clinical device 30. A third sensor 38 may also be provided and allows for additional verification of patient compliance or other data to be collected as the patient wears the active clinical device 30. For example, the third sensor 38 may be still another pressure sensor placed in a different location within the active clinical device 30 to provide a more reliable reading or verification that the patient is indeed wearing the device 30. So another example of a possible sensor 38 would be a small mechanical snap switch or the like which would have a slight pressure actuator such that as the device is mechanically positioned on the patient's body, this sensor 38 is actuated and again provides an indication that the patient is wearing the device. Still other possibilities for sensor 38 may be envisioned as would be apparent to those of skill in the art.

In use, as the patient properly applies the active clinical device 30 to her body, one or more of the sensors 34–38 are actuated and provide an electrical signal to the controller 22. Controller 22 may associate this signal with a time stamp provided by clock 24 and thus keep track of or time the amount of elapsed time that the patient has the active clinical device 30 in an operative mode on her body. This collective data may then be stored in memory 26 through various regimens and protocols to provide a body of data corresponding to the patient's compliance. Then, at any desired time or, upon demand, or in response to query, or otherwise as desired, a communication link 40 may be used to transfer the data stored in memory 26 through controller 24 and through an output port to download data to a central office or otherwise for data collection, analysis, and other purposes as may be desired. Ultimately, it would be anticipated that this patient compliance data may be used to counsel the patient to encourage her as she makes use of the medical device 30. For example, should a patient exhibit minimal compliance, the patient may be provided that feedback and become aware that the device itself has a means of tracking her usage. Such knowledge of tracking may itself encourage the patient to become more compliant. Furthermore, patient compliance may then also be used as a parameter to determine the relative efficacy of the medical device 30 and its correlation to the degree of patient compliance with a recommended regimen or even independently of same.

Various changes and modifications to the invention may be apparent to those of ordinary skill in the art, and those changes and modifications are intended to be Included within the scope of the invention. This invention should be limited by only the scope of the claims appended hereto and their equivalents.

What is claimed is:

1. A medical appliance for soft tissue enlargement having a patient monitoring device comprising at least a first sensor to sense a patient biological parameter, said patient biological parameter being directly indicative of the patient's contemporaneous use of the soft tissue enlargement appliance, said first sensor being connected to and supplying first sensor output data to a controller, said first sensor output data corresponding to said sensed patient biological parameter, the controller being configured to correlate said first sensor output data with time to thereby generate compliance data, and said controller including a download port for outputting said compliance data.

2. The soft tissue enlargement appliance of 1 further comprising a timer associated with the controller for providing a time correlation to said first sensor output data.

3. The soft tissue enlargement appliance of claim 2 further comprising an electromechanical device for applying a force to the patient, and a second sensor for sensing the output of said electromechanical device, the second sensor being connected to said controller and supplying second sensor output data thereto for correlation with time to thereby generate compliance data.

4. The soft tissue enlargement appliance of claim 3 wherein said soft tissue enlargement appliance is worn by said patient, and wherein said first sensor comprises a temperature sensor positioned to sense the patient's temperature as the soft tissue enlargement appliance is worn to thereby provide an indication of contemporaneous patient use.

5. The soft tissue enlargement appliance of claim 4 further comprising a memory associated with said controller for storing said compliance data prior to download through said download port.

6. The soft tissue enlargement appliance of claim 5 wherein said electromechanical device comprises a pump for creating a negative pressure within a dome, and said second sensor comprises a pressure sensor for sensing the negative pressure created by said pump.

7. The soft tissue enlargement appliance of claim 6 further comprising a third sensor, said third sensor being adapted and positioned to sense another device parameter and being connected to said controller for transmitting third sensor output data thereto for correlation with time to thereby generate compliance data.

8. A medical appliance worn by a patient, said medical appliance having a patient monitoring device comprising an electromechanical device, a pressure sensor, and a temperature sensor, said electromechanical device comprising a pump for creating a negative pressure within a dome, said pressure sensor for sensing the negative pressure created by said pump, said temperature sensor being positioned to sense the patient's temperature as said medical device is worn to thereby provide an indication of contemporaneous use of said medical appliance by the patient, said pressure sensor being connected to and supplying pressure sensor output data to a controller, said temperature sensor being connected to and supplying temperature sensor data to said controller, said controller having a timer and a memory associated therewith, said timer for producing time data and said memory for storing said data collected by said controller prior to download through a download port, the controller being configured to correlate said temperature sensor output data and said pressure sensor output data with the time data to thereby generate compliance data, and said controller including said download port for outputting said compliance data.

9. The medical appliance of claim 8 further comprising a third sensor, said third sensor being adapted and positioned to sense another device parameter and being connected to said controller for transmitting third sensor output data thereto for correlation with time to thereby generate compliance data.

10. A soft tissue enlargement device adapted for being worn by a patient in order to administer a prescribed protocol, said device having (1) a pair of vacuum domes for applying a tension to a patient's soft tissue, each of said domes being adapted to enclose a female patient's breast, (2) a sensor for determining when the domes are applying a tension to the patient's soft tissue, (3) a patient monitor having a temperature sensor and a controller, the temperature sensor being positioned for being heated by said patient as the device is worn to thereby provide an indication that said device is being worn, said controller for collecting and storing data from said sensor associated with said tensioning applicator and said temperature sensor, said controller having a microprocessor, a memory, and a download port, said download port for transferring said data collected by said controller out of said device, said patient monitor for determined if and for how long a patient wears said device as prescribed, and (4) a timer for correlation with said temperature sensor output to thereby provide data corresponding to how long said patient is wearing the device.

* * * * *

UNITED STATES PATENT AND TRADEMARK OFFICE
CERTIFICATE OF CORRECTION

PATENT NO.     : 6,514,200 B1
DATED          : February 4, 2003
INVENTOR(S)    : Roger K. Khouri It is certified that error appears in the above-identified patent and that said Letters Patent is hereby corrected as shown below:

<u>Column 6,</u>
Lines 12-13, please replace the word "determined" with the word -- determining --.

Signed and Sealed this

Fifth Day of October, 2004

JON W. DUDAS
*Director of the United States Patent and Trademark Office*